(12) United States Patent
Sattur et al.

(10) Patent No.: US 7,056,707 B2
(45) Date of Patent: Jun. 6, 2006

(54) BIOACTIVE COMPOUND AND ITS ISOLATION AND METHOD OF TREATMENT FOR LIPOXYGENASE INHIBITION AND AS FREE RADICAL SCAVENGING AGENT

(75) Inventors: Avinash Prahlad Sattur, Karnataka (IN); Chandrasekhar Rao Kadiyala, Karnataka (IN); Divakar Soundar, Karnataka (IN); Karanth Naikanakatte Ganesh, Karnataka (IN); Tumkur Ramachandraiah Shamala, Karnataka (IN); Appu Rao Appu Rao Gopal Rao, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 128 days.

(21) Appl. No.: 10/724,999

(22) Filed: Dec. 2, 2003

(65) Prior Publication Data

US 2004/0225012 A1 Nov. 11, 2004

Related U.S. Application Data

(63) Continuation-in-part of application No. 10/107,807, filed on Mar. 28, 2002, now abandoned.

(51) Int. Cl.
- *C12P 13/02* (2006.01)
- *A61K 31/195* (2006.01)
- *C07C 233/64* (2006.01)

(52) U.S. Cl. ................ 435/129; 435/254.3; 435/256.1; 514/563; 562/444; 562/450; 562/455

(58) Field of Classification Search ................ 435/129, 435/254.3, 256.1; 562/444, 450, 455; 552/450, 552/455; 514/563
See application file for complete search history.

(56) References Cited

U.S. PATENT DOCUMENTS 6,294,186 B1 * 9/2001 Beerse et al. ................ 424/405

* cited by examiner

*Primary Examiner*—Herbert J. Lilling
(74) *Attorney, Agent, or Firm*—Venable LLP; Ann S. Hobbs

(57) ABSTRACT

The present invention relates to a novel compound having a molecular formula $C_{13}H_{15}NO_5$ having molecular structure of Formula I and a process for the isolation of said compound. The present invention also relates to a method of inhibiting 13-lipoxygenase and having free radical scavenging activity.

23 Claims, 3 Drawing Sheets

BIOACTIVE COMPOUND AND ITS ISOLATION AND METHOD OF TREATMENT FOR LIPOXYGENASE INHIBITION AND AS FREE RADICAL SCAVENGING AGENT

This application is a continuation-in-part of application Ser. No. 10/107,807, filed Mar. 28, 2002, now abandoned the entire contents of which are hereby incorporated by reference.

FIELD OF INVENTION

The present invention relates to a novel compound having a molecular formula $C_{13}H_{15}NO_5$ having molecular structure 1 and a process for the isolation of said compound. The present invention also relates to a method of inhibiting 13-lipoxygenase and having free radical scavenging activity.

BACKGROUND AND PRIOR ART REFERENCES

Lipids are highly vulnerable to oxidation, which can be initiated by enzymatic and non-enzymatic processes. The enzymatic process is initiated by lipoxygenases, which are responsible for the oxygenation of polyunsaturated fatty acids such as linoleic, linolenic and arachadonic acid.

These enzymes are found to be responsible for the deterioration, rancidity and loss of flavor in food materials and also for various diseases in the human body, such as Parkinson's disease, cataractogenesis, endotoxin liver injury, and myocardial infarction. (Began G, Sudharshan E and Appu Rao AG Lipids 33 (1998) 1223–1228; Sics H (ed.) Oxidative State, Oxidants and Antioxidants, pp-8, Academic Press, London (1991)). Inhibitors against these enzymes thus have a potential application in both the food and medical sector.

The use and manufacture of various antioxidants have been reviewed by Madhavi, D L and Salunkhe, D K (1994) In Food Additive Toxicology, Maga, J A and Tu, A T (eds) Marcel Dekker, NY 88–177.

Allgayer et al (1984) have reported that therapeutically active compound such as sulphasalazine metabolites are soybean lipoxygenase inhibitors (Allgayer H, Eisenburg J and Paumgartner G Eur J Clin Pharmacol 26 (1984) 449–451)

OBJECTS OF THE PRESENT INVENTION

The main object of the present invention is to provide a novel bioactive compound having molecular formula $C_{13}H_{15}NO_5$ with molecular structure 1.

The main object of the present invention is to provide a novel bioactive compound 2-amido, 3-hydroxy, 4-propene, 5-methyl, 6-methoxy benzoic acid.

An object of the present invention is to provide a process for the isolation of said compound.

Yet another object of the present invention is to provide a method of treatment to inhibit lipoxygenase enzyme and for the treatment of asthma, hypersensitivity, psoriasis, inflammatory conditions and complications arising out of diabetes and also as free radical scavenging activity.

SUMMARY OF THE INVENTION

To meet the above objectives, the present invention provides a novel compound having molecular formula $C_{13}H_{15}NO_5$ with molecular structure 1. The present invention also provides a process for the isolation of said compound from *Aspergillus niger* and a method treatment in inhibiting 13-Lipoxygenase inhibitor, in scavenging of free radicals, for the treatment of asthma, hypersensitivity, psoriasis, inflammatory conditions and complications arising out of diabetes.

DETAILED DESCRIPTION OF THE INVENTION

Figure 1:
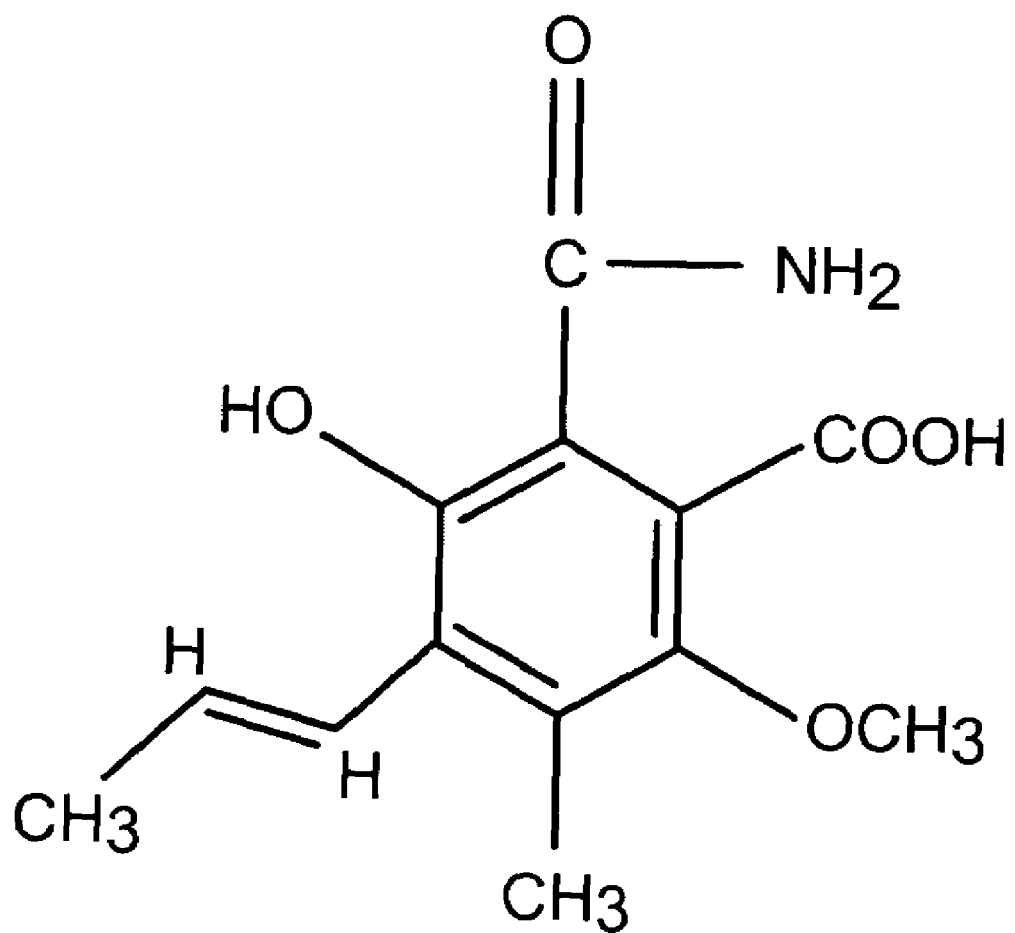
FIG. 1: Molecular structure of the compound having a molecular formula $C_{13}H_{15}NO_5$
Figure 2:
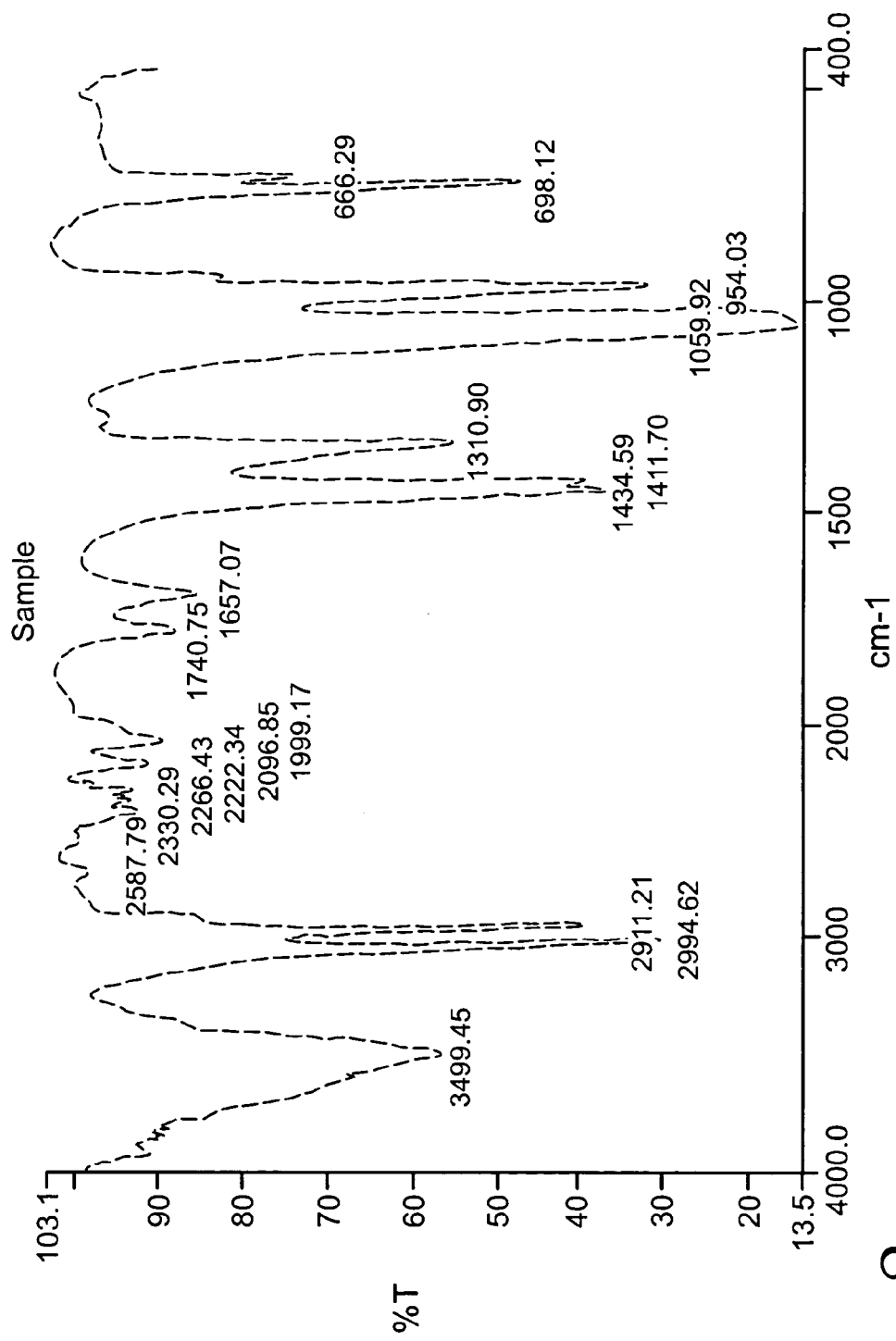
FIG. 2: IR spectrum of Compound having FIG. 1
Figure 3:
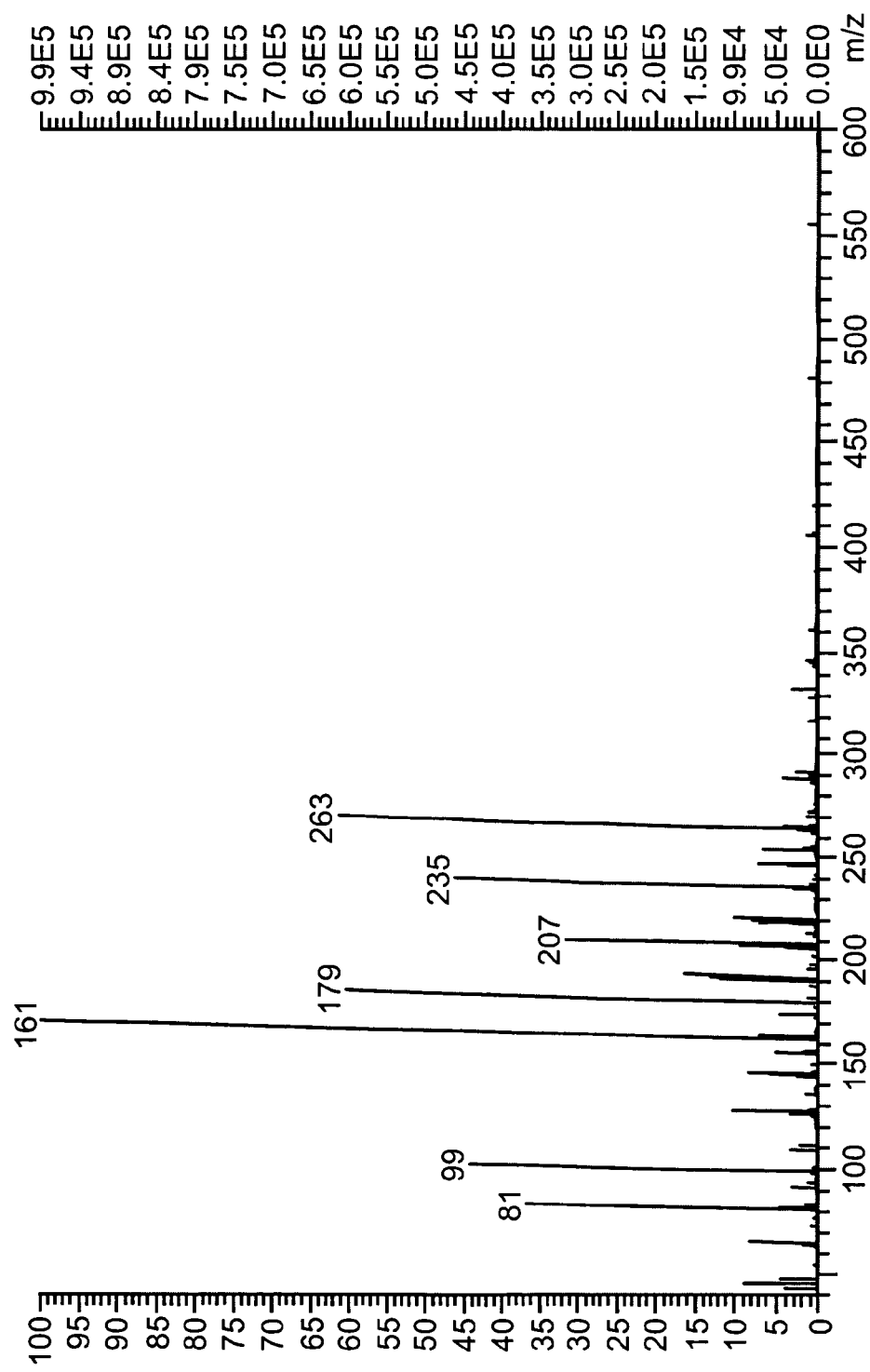
FIG. 3: H-NMR spectral data of Compound having FIG. 1
Figure 1:
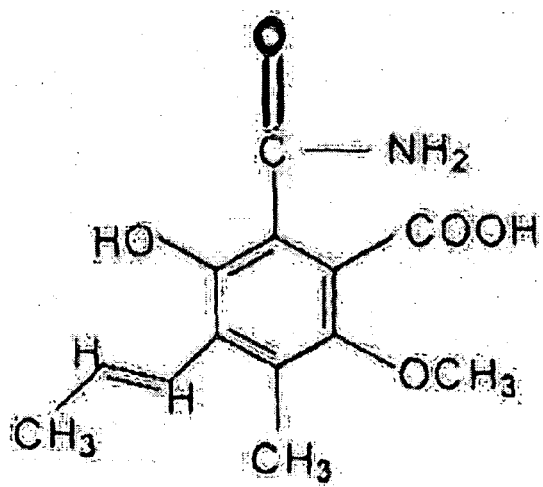

Accordingly, the present invention provides a bioactive compound isolated from the culture of *Aspergillus Niger*, said compound having a molecular formula $C_{13}H_{15}NO_5$ having a molecular structure 1:

Yet another embodiment of the present invention, wherein said compound is soluble in an organic solvent selected from the group consisting of ethanol, methanol, ethyl acetate, and dimethyl sulphoxide.

Still another embodiment of the present invention, wherein said compound is sparingly soluble in chloroform and hexane, but insoluble in water.

Yet another embodiment of the present invention, wherein said compound is soluble in aqueous alkaline solution selected from sodium bicarbonate, sodium carbonate and potassium bicarbonate and potassium carbonate and sodium hydroxide, lithium hydroxide and potassium hydroxide.

An embodiment of the present invention, wherein said compound having a basic skeleton of benzene ring having substituents hydroxyl, methyl, carboxyl, carboxamide, methoxyl and propenyl groups.

Further embodiment of the present invention, wherein said compound having the physical characteristics as given below:

Nature: yellow amorphous powder.
Melting Point: 253° C.
$\lambda_{max}$ nm ($\epsilon$) in methanol: 235(20,700), 292 (11,600), 358 (4,400)
IR: 3499, 1657, 2994 cm$^{-1}$.
Molecular formula: $C_{13}H_{15}NO_5$
EI-MS m/z: 265 (M$^+$) 263 [M$^+$–2H, 60%] 235 [M$^+$ —(CH$_3$—CH—), 45%] 207 [235 —(CH$_3$—C$_{Ar}$, 30%] 163 (207 —CO$_2$, 49%) 161 [100%] 99 [45%] 81 [37%]
$^1$H NMR spectra ($\delta$, ppm): 2.04 (3H, d, J=6.6 Hz, CH$_3$—CH=CH—) 6.61 (1H, dq, J=16.4 Hz, 6.9 Hz, CH$_3$—CH=C) 6.69 (1H, d, J=16.4 Hz, HC=CH—Ar) 2.02 (S) (3H, s, Ar—CH$_3$) 3.43 (S) (3H, s, Ar—OCH$_3$) 10.3 (Ar—OH) 11.5 (Ar—COOH)
$^{13}$C NMR spectra ($\delta$, ppm):

| | | | |
|---|---|---|---|
| CH$_3$ | 15.0 | =C—C$_{Ar}$ | 167 |
| =CH | 122 | —COOH | 161 |
| =CH | 134 | C$_{Ar}$—O—CH$_3$ | 149.5 |
| —CH$_3$ | 15.0 | C$_{Ar}$—OH | 148 |
| C$_{Ar}$—CH$_3$ | 117 | CONH$_2$ | 168 |

The present invention also provides a pharmaceutical composition for Lipoxygenase inhibition and free radical scavenging activity, in subjects, said composition comprising an effective amount of the said bioactive compound having a molecular formula $C_{13}H_{15}NO_5$ along with pharmaceutically accepted excipients.

An embodiment of the present invention wherein said composition is used to treat asthma, hypersensitivity, psoriasis, inflammatory conditions and complications arising out of diabetes.

An embodiment of the present invention, the pharmaceutical composition wherein the excipients are selected from the group consists of carriers, colorants, flow modifiers and stabilizers.

Yet another embodiment of the present invention, the pharmaceutical composition wherein the excipients used are in the suitable amounts ranging between 0.001–0.99wt %.

Still another embodiment of the present invention, wherein said composition is used in the form of oral, parental, nasal, topical, buccal and ocular.

Yet another embodiment of the present invention, wherein the subject is selected from mammals.

The present invention also provides a process for the isolation of compound with molecular formula $C_{13}H_{15}NO_5$, said process comprising the steps of:

(a) isolating the strain CFR-W-105 from *Aspergillus niger* V. Teigh from honey bee wax;

(b) propagating the strain obtained from step(a) on a Potato Dextrose Agar medium and incubating for 4 days at 30° C.;

(c) inoculating with a slant of step (b) into seed liquid medium contained in Erlenmeyer flask;

(d) incubating the liquid medium of step (c) in Erlenmeyer flask at 30° C. on a rotary shaker at 250 rpm to obtain the seed culture;

(e) transferring the culture of step (d) into Erlenmeyer flasks containing wheat bran, mineral acid, sulfates and incubated for 5 days at 30° C. to obtain fermented wheat bran;

(f) treating the fermented wheat bran of step (e) with an organic solvent for two hours to obtain an organic solvent extract;

(g) separating the organic solvent extract of step(f) from the wheat bran by cheese cloth filtration;

(h) drying the organic layer of step (g) over anhydrous sodium sulfate and concentrating under reduced pressure to obtain a solid;

(i) suspending the solid of step (h) in an organic solvent and centrifuging to obtain a residue;

(j) drying the residue of step (i) to obtain an orange solid;

(k) dissolving the solid of step (j) in an alcoholic solvent;

(l) treating the solution of step(k) with active charcoal, filtering; and (m) concentrating the filtrate under reduced pressure to obtain a novel compound of molecular formula $C_{13}H_{15}NO_5$ having molecular structure 1 as yellow amorphous powder.

An embodiment of the present invention, the process wherein the seed liquid medium is selected from Czapex solution agar for Carbon source and Czapex solution agar replacing sodium nitrate for nitrate source.

Another embodiment of the present invention, the process wherein the mineral acid that is used for flask fermentation in step (e) is hydrochloric acid.

Yet another embodiment of the present invention, the process wherein the organic solvent used in step (f) is selected from the group consisting of dichloromethane, chloroform, ethylacetate, methylisobutyl ketone and preferably ethylacetate. Still another embodiment of the present invention, the process wherein the organic solvent used for suspending the residue in step (i) is chloroform.

The present invention further provides a method of treating subjects with pharmaceutical composition comprising a bioactive compound of molecular formula $C_{13}H_{15}NO_5$ along with pharmaceutically accepted excipients used for treatment of 13-Lipoxygenase inhibition and having free radical scavenging activity.

An embodiment of the present invention the method wherein said composition is used to treat asthma, hypersensitivity, psoriasis, inflammatory conditions and complications arising out of diabetes.

Yet another embodiment of the present invention the method wherein said compound having 13-lipoxygenase and crude rat lens aldose reductase inhibitory activity.

Still another embodiment of the present invention the method wherein the subject is selected from mammals.

Yet another embodiment of the present invention the method wherein the IC$_{50}$ value of the compound against purified soybean lipoxygenase and crude rat lens aldose reductase inhibitory activity is 79 µmoles and 69 µmoles respectively.

Further embodiment of the present invention the method wherein ED$_{50}$ value of the composition for free radical scavenging activity is 66 µM.

DETERMINATION OF MOLECULAR STRUCTURE

The compound exhibited UV absorption maxima at 235, 292 and 358 nm. Of these the 292 nm band corresponds to the phenolic absorption. The 358 nm band indicates extent conjugation involving the aromatic ring. The broad IR absorption at 3499 cm$^{-1}$ indicates OH./NH2 stretching frequencies. Similarly, the 1657 cm$^{-1}$ band indicates the carbonyl (—CO—) stretching frequency of an acid. The —CH— aromatic stretching is indicated by the 2994 cm$^{-1}$ band. Further, conformation of the structure was obtained from multiple quantum coherence transfer spectra (MQCT). The signals at 2.04 (doublet) and 2.02 ppm indicates —CH$_3$ attached to olefinic double bond or an aromatic ring. The olefinic protons at 6.61 and 6.69 which corresponds to only two protons posses characteristic splitting of an olefinic group attached to an aromatic ring. The signal at 6.69 ppm which is a doublet with 16.4 Hz coupling constant indicates that trans proton of an olefinic group. Correspondingly, the signal at 6.61 ppm (doublet of a quartet) with 16.4 and 6.90 Hz coupling indicate that this trans proton is coupled to the olefinic proton at 6.61 ppm and to a —CH$_3$ group attached to the same carbon. These characteristics indicate the presence of a CH$_3$CH═CH— group, this olefinic double bond was further conformed by decoloration of bromine-water. A singlet at 3.43 ppm indicate —OCH$_3$ group. A —OH signal at 10.3 ppm and carboxyl proton at 11.5 ppm indicates that these groups are present probably on the aromatic ring. The Lassaigne's, sodium test indicate that the presence of nitrogen which is probably present in the form of an amide, this was conformed by detecting the evolution of ammonia, upon heating with sodium hydroxide solution, indicating that nitrogen is present as amide. MQCT spectra also gave corresponding carbon signals where ever protons are attached. The table shows the chemical shift values of the carbon signals detected. The structure of compound arrived from spectroscopic data was further conformed by GC-EIMS analysis. A parent ion peat at 263 (M$^+$ −2H) was observed. Other fragmented peaks like 235 (263 —CH$_3$CH═), 207 (—CH$_3$—C$_{Ar}$), 163 (207 —COO$^-$), 99, 81 etc. also conformed the proposed structure of compound 1. Based on this data the proposed structure of compound is shown in FIG. 1.

The invention is further explained in the form of following embodiments Applicants have discovered a antibiotic 13-LOX inhibitory compound which are derived via the fermentation of certain microorganisms.

*Aspergillus Niger* CFR-W-105 isolated from a wax sample is found to produce new biologically active substance. This substance is extracted from the fermented wheat bran using ethyl acetate followed by crystallization. The purified compound is identified as compound having a molecular formula C$_{13}$H$_{15}$NO$_5$.

Thus the fermentation of *Aspergillus Niger* CFR-W-105 or a mutant thereof and suitable isolation techniques may be used to produce the compound of the investigation.

A biologically pure culture of *Aspergillus niger* CFR-W-105, from which the compound of investigation is derived, has been deposited with the Microbial Type Culture Collection (MTCC) in Chandigarh, India, and has been added to its permanent collection under its accession code MTCC 5116.

Taxonomy

Morphology

The fungal mycelium on czapek's solution agar had abundant erect and crowded conidial structures, which is brownish black or dark brown covering the entire colony except for the narrow peripheral growing area. Conidial heads are globose initially, which slowly split into radiating columns at the end of 10 days. Sclerotia are not observed.

Cultural and Physiological Characteristics

The growth characteristics of CFR-W-105 on malt-extract-agar are similar to that of Czapek's solution agar. But the colonies are deeper brownish black, reverse of the plate is uncolored and unwrinkled and conidiophores are less dense. Growing margin is less prominent. The culture grew well at ambient temperature of 26°–30° C. conidia is born by biseriate sterigmata (25–30^) and are 2.5–4.5 n in size and globose at maturity. The walls are smooth arid thick. The length of conidiophores is 0.7–1.0 mm. Table 1 shows the growth of CRF-W-105 in the presence of various carbon and nitrogen sources.

TABLE 1

Growth of CFR-W-105 in the presence of various carbon and nitrogen sources.

| C-Source | growth | reverse side color Of the plate | spores |
|---|---|---|---|
| Sucrose | good, wrinkled | yellow | dark brown, dense |
| Maltose | good, less wrinkled | none | dark brown, dense |
| Glucose | good, wrinkled | slight yellow | dark brown, dense |
| Fructose | good, less wrinkled | yellow | dark brown, dense |
| Cellobiose | good, less wrinkled | brown | dark brown, dense |
| Inositol | less, not wrinkled | none | dark brown scanty |
| Rhamnose | good, not wrinkled | yellow | very dark black, dense |
| Mannitol | less, not wrinkled | yellow | dark brown, less dense |
| Xylose | good, not wrinkled | yellow | dark brown, dense |
| Arabinose | less, not wrinkled | yellow | light brown, less dense |
| N-Source | | | |
| Ammonium Sulfate | good, wrinkled | yellow | dark brown, less dense |
| Ammonium Nitrate | good, wrinkled | yellow | dark brown, centrally situated |
| Sodium Nitrate | good, wrinkled | yellow | dark brown, dense |
| Ammonium Chloride | good, wrinkled | yellow | dark brown, centrally situated, less dense |

The basal medium of the above experiments contained Czapex solution agar for Carbon source and Czapex solution agar replacing sodium nitrate for nitrate source.

Taxonomic Position

The strain CFR-W-105 is isolated from honeybee wax from local region. The characteristics indicated that the strain belongs to *Aspergillus Niger* group. According to the descriptions of Raper and Fennell (Raper K B and Fennell D T (1965) The Genus *Aspergillus*; The Williams and Wilkins Co, Baltimore, pp 293–310), the strain CFR-W-105 is related to *Aspergillus niger* V. Tiegh.

The taxonomic relationships between the strains and four other cultures that did not give the bioactive molecules during screening are compared and given in Table 2.

TABLE 2

Comparison between the strains CFR-W-105 and three other related species which did not give the compound I (as on Czapex solution agar, 26–28° C., 10 days)

| Strain | growth | reverse side color Of the plate | spores |
|---|---|---|---|
| NRRL-330 | good, wrinkled | less yellow | dark brown, dense |
| NRRL-337 | good, wrinkled | none | dark brown, dense |
| CFR-1046 | less, less wrinkled | none | dark brown, dense |
| CFR-18 | good, wrinkled | less yellow | dark brown, dense |
| CFR-W-105 | good, less wrinkled | yellow | less dark brown, less dense |

Fermentation

Seed Culture

Strain CFR W-105 is propagated on Potato Dextrose Agar (Hi Media Mumbai, India) slant composed of soluble starch 0.4% and glucose 2%. After incubation for 4 days at 30° C., a portion of the mature agar slant is inoculated into 100 ml of a seed liquid medium of the same medium composition in a 500-ml Erlenmeyer flask and incubated at 30° C. on a rotary shaker at 250 rpm.

Flask Fermentation

A 5-ml of the seed culture is transferred into 250-ml Erlenmeyer flasks each containing 10 gm of wheat bran, 10 ml of 0.2 N HCl comprising 2.1 mg each of ferrous sulfate, zinc sulfate and copper sulfate and 5 ml distilled water. The inoculated flasks are incubated for 5 days at 30° C. Isolation and Purification.

The fermented wheat bran (450 g) is treated with ethyl acetate (1 liter) for two hours. The organic extract is separated from the wheat bran by cheesecloth filtration. This extract is dried over anhydrous sodium sulfate and concentrated in vacuo to afford a crude solid (1.36 gm) and the residue is resuspended in chloroform (25 ml) and gently centrifuged (2000 rpm, 20 minutes, 27° C.). The residue is dried to afford an orange colored active fraction (230-mg). This is dissolved in ethyl alcohol (50 ml) by gentle warming and treated with activated charcoal (200 mg) filtered (Whatman No.1) while warm. The filtrate is concentrated in vacuo to obtain 30 mg of yellow amorphous powder.

Physico-chemical Properties

The compound is amorphous yellow powder. It is soluble in ethanol, methanol, ethyl acetate, dimethyl sulphoxide, sodium bicarbonate solution, sodium carbonate solution and sodium hydroxide solution, slightly soluble in chloroform and hexane, but insoluble in water. The EI-MS spectra of the compound showed the molecular ions at m/z 265.

Compositions and Methods

The novel compounds of the invention can be used in a variety of pharmaceutical dosage forms. Thus, oral, parental, nasal, topical, buccal, ocular and other forms can be used. When such forms are formulated they will include pharmaceutically acceptable excipients such as colorants, carriers, perfumes, stabilizers, flow modifiers and the like in suitable amounts (i.e., from 0.001 to 0.99wt %).

The compound of the invention is useful in methods of inhibiting the effects of 13-LOX.

The compound is also used to treat a host, preferable a mammal, which is suffering from a disorder associated with a metabolism of 13-LOX, such as asthma, hypersensitivity, psoriasis, inflammatory conditions and complications arising from diabetes.

The following example illustrates the 13-Lipoxygenase inhibitor effects of the novel compound, however this shall not be considered as limiting the scope of the invention.

EXAMPLE

Soybean lipoxygenase (LOX-1) is purified according to the method of Axelrod et al., lipoxygenase from soybeans. Methods in Enzymology 1981, 71, 441–451, using the Hardee variety of soybean, after dehulling and defatting by hexane. The substrate, sodium linoleate (10 mM) is prepared as follows:

To 70 mg of linoleic acid an equal weight of Tween-20 and 4 ml of oxygen free water is added and homogenized by drawing back and forth in a pasture pipette, avoiding air bubbles. Sufficient quantity of 0.5 N NaOH is added to this to yield a clear solution. The resulting sodium linoleate is divided into 1–2 mL portions in small screw cap vials, flushed with $N_2$ before closing, and keep frozen until needed. Enzyme reaction is carried out at 25° C. in a quartz cuvette with a 1 cm light path. The assay mixture contained (2.975–x) ml of borate buffer (0.2 M, pH 9.0), 0.025 ml of sodium linoleate substrate, and x mL of enzyme. After each addition the mixture is stirred with a few strokes of a plastic paddler. The reference cuvette contained no enzyme. Absorption at 234 nm is recorded, and the reaction rate is determined from the slope of the straight-line portion of the curve.

Lens are collected from rat eyes and homogenised with sodium, potassium phosphate buffer (0.135 M, pH 7.0) containing 0.5 mM of phenyl methyl sulphonyl fluoride and 10 mM of p-mercaptoethanol. The homogenate is centrifuged at 10,000 r.p.m for 30 minutes at 4° C. The supernatant is taken as enzyme source. Enzyme reaction is carried out at 25° C. in a quartz cuvette with a 1-cm light path. The assay mixture contained 100 µL of nicotinamide adenine dinucleotide phosphate tetra sodium salt (from a stock solution of 9.6 mM), 100 µL of DL-glyceraldehyde (from a stock solution of 250 mM), 10 µL of inhibitor dissolved in dimethyl sulphoxide, sodium-potassium-phosphate buffer (0.135 M, pH 7.0) to make up the total volume to 3 µL and the reaction is initiated by the addition of 200 µL of enzyme solution. The enzyme reaction is monitored by the decrease in absorbency at 340 nm and compared with enzyme reaction without inhibitor.

Results

The bioactive compound having molecular formula $C_{13}H_{15}NO_5$ is discovered in the fermented bran of a species of *Aspergillus Niger* CFR W-105. The compound is successfully purified to homogeneity. The $IC_{50}$ value of the compound against purified soybean lipoxygenase and crude rat lens aldose reductase inhibitory activity is determined to be 79 n moles and 69 n moles respectively.

The invention claimed is:

1. A bioactive compound isolated from the culture of *Aspergillus Niger*, said compound having a molecular formula $C_{13}H_{15}NO_5$ with molecular structure 1:

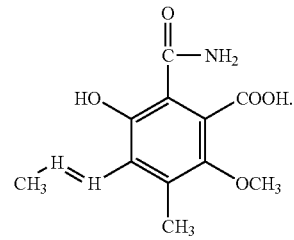

Formula 1

2. The compound according to claim 1, wherein the molecular structure 1 having molecular formula $C_{13}H_{15}NO_5$ is 2-amido, 3-hydroxy, 4-propene, 5-methyl, 6-methoxy benzoic acid.

3. The compound according to claim 1, wherein said compound is soluble in an organic solvent selected from the group consisting of ethanol, methanol, ethyl acetate and dimethyl sulphoxide.

4. The compound according to claim 1, wherein said compound is sparingly soluble in chloroform and hexane, but insoluble in water.

5. The compound according to claim 1 wherein said compound is soluble in aqueous alkaline solution selected from sodium bicarbonate, sodium carbonate and potassium bicarbonate and potassium carbonate and sodium hydroxide, lithium hydroxide and potassium hydroxide.

6. The compound according to claim 1 wherein said compound having the physical characteristics as given below:
Nature: yellow amorphous powder:
Melting Point: 253° C.
$\lambda_{max}$ nm ($_\epsilon$) in methanol: 235(20,700), 292 (11,600), 358 (4,400)
IR: 3499, 1657, 2994 cm$^{-1}$
Molecular formula: $C_{13}H_{15}NO_5$
EI-MS m/z:265 (M$^+$) 263 [M$^+$-2H, 60%] 235 [M$^+$—(CH$_3$—CH—), 45%] 207 [235 —(CH$_3$—C$_{Ar}$, 30%] 163 (207 —CO$_2$, 49%) 161 [100%] 99 [45%] 81 [37%]
$^1$H NMR spectra (δ, ppm): 2.04 (3H, d, J=6.6 Hz, C$\underline{H}_3$—CH=CH—) 6.61 (1H, dq, J=16.4 Hz, 6.9 Hz, C$\underline{H}_3$—C$\underline{H}$=C) 6.69 (1H, d, J=16.4 Hz, HC=C$\underline{H}$—Ar) 2.02 (S) (3H, s, Ar—C$\underline{H}_3$) 3.43 (S) (3H, s, Ar—OCH$_3$) 10.3 (Ar—O$\underline{H}$) 11.5 (Ar—COO$\underline{H}$)
$^{13}$C NMR spectra (δ, ppm):

| CH$_3$ | 15.0 | =C—C$_{Ar}$ | 167 |
| =CH | 122 | —COOH | 161 |
| =CH | 134 | C$_{Ar}$—O—CH$_3$ | 149.5 |
| —CH$_3$ | 15.0 | C$_{Ar}$—OH | 148 |
| C$_{Ar}$—CH$_3$ | 117 | CONH$_2$ | 168. |

7. A pharmaceutical composition comprising a bioactive compound of molecular formula $C_{13}H_{15}NO_5$ with molecular structure 1, along with pharmaceutically accepted excipients used for treatment of 13-Lipoxygenase inhibition and having free radical scavenging activity in subjects.

8. A pharmaceutical composition according to claim 7, wherein said composition is used to treat asthma, hypersensitivity, psoriasis, inflammatory conditions and complications arising out of diabetes.

9. The pharmaceutical composition according to claim 7, wherein the pharmaceutical excipients are selected from the group consisting of carriers, colorants, flow modifiers and stabilizers.

10. The pharmaceutical composition according to claim 7, wherein the excipients used are in the suitable amounts ranging between 0.001–0.99wt %.

11. The pharmaceutical composition according to claim 7, wherein said composition is used in the form of oral, parental, nasal, topical, buccal and ocular.

12. The pharmaceutical composition according to claim 7, wherein the subject is selected from mammals.

13. A process for the isolation of bioactive compound having a molecular formula $C_{13}H_{15}NO_5$ with molecular structure 1, said process comprising the steps of:
(a) isolating the strain CFR-W-105 from *Aspergillus niger* V. *Teigh* from honey bee wax;
(b) propagating the strain obtained from step(a) on a Potato Dextrose Agar medium and incubating for 4 days at 30° C.;
(c) inoculating with a slant of step (b) into seed liquid medium contained in Erlenmeyer flask;
(d) incubating the liquid medium of step (c) in Erlenmeyer flask at 30° C. on a rotary shaker at 250 rpm to obtain the seed culture;
(e) transferring the culture of step (d) into Erlenmeyer flasks containing wheat bran, mineral acid, sulfates and incubated for 5 days at 30° C. to obtain fermented wheat bran;
(f) treating the fermented wheat bran of step (e) with an organic solvent for two hours to obtain an organic solvent extract;
(g) separating the organic solvent extract of step (f) from the wheat bran by cheese cloth filtration;
(h) drying the organic layer of step (g) over anhydrous sodium sulfate and concentrating under reduced pressure to obtain a solid;
(i) suspending the solid of step (h) in an organic solvent and centrifuging to obtain a residue;
(j) drying the residue of step (i) to obtain an orange solid;
(k) dissolving the solid of step (j) in an alcoholic solvent;
(l) treating the solution of step (k) with active charcoal, filtering; and
(m) concentrating the filtrate under reduced pressure to obtain compound having a molecular formula $C_{13}H_{15}NO_5$ having molecular structure 1, as yellow amorphous powder.

14. The process according to claim 13 wherein the seed liquid medium is selected from Czapex solution agar for Carbon source and Czapex solution agar replacing sodium nitrate for nitrate source.

15. The process according to claim 13 wherein the mineral acid used for flask fermentation in step (e) is hydrochloric acid.

16. The process according to claim 13 wherein the organic solvent used in step (f) is selected from the group consisting of dichloromethane, chloroform, ethylacetate, methylisobutyl ketone and preferably ethylacetate.

17. The process according to claim 13 wherein the organic solvent used for suspending the residue in step (i) is chloroform.

18. The method of treating subjects with pharmaceutical composition comprising a bioactive compound of molecular formula $C_{13}H_{15}NO_5$ along with pharmaceutically accepted excipients used for treatment of 13-Lipoxygenase inhibition and having free radical scavenging activity.

19. The method according to claim 18 wherein said composition is used to treat asthma, hypersensitivity, psoriasis, inflammatory conditions and complications arising out of diabetes.

20. The method according to claim 18 wherein said compound having 13-lipoxygenase and crude rat lens aldose reductase inhibitory activity.

21. The method according to claim 18 wherein the subject is selected from mammals.

22. The method according to claim 18 wherein the IC$_{50}$ value of the compound against purified soybean lipoxygenase and crude rat lens aldose reductase inhibitory activity is 79μ moles and 69μ moles respectively.

23. The method according to claim 18 wherein ED$_{50}$ value of the composition for free radical scavenging activity is 66 μM.

* * * * *